United States Patent [19]
Khosravi et al.

[11] Patent Number: 5,618,299
[45] Date of Patent: *Apr. 8, 1997

[54] RATCHETING STENT

[75] Inventors: Farhad Khosravi, Belmont, Calif.; Michael S. Williams, Chapel Hill, N.C.

[73] Assignee: Advanced Cardiovascular Systems, Inc., Santa Clara, Calif.

[ * ] Notice: The term of this patent shall not extend beyond the expiration date of Pat. No. 5,441,515.

[21] Appl. No.: 512,300

[22] Filed: Aug. 8, 1995

Related U.S. Application Data

[62] Division of Ser. No. 52,410, Apr. 23, 1993, Pat. No. 5,441,515.

[51] Int. Cl.$^6$ .................................................. A61M 29/00
[52] U.S. Cl. .......................................... 606/198; 606/191
[58] Field of Search ..................... 606/1, 108, 190–198; 623/1, 11, 12

[56] References Cited

U.S. PATENT DOCUMENTS

| | | |
|---|---|---|
| 2,361,506 | 10/1944 | Smith . |
| 3,657,744 | 4/1972 | Ersek . |
| 4,089,006 | 2/1992 | Stiles . |
| 4,130,904 | 12/1978 | Whalen . |
| 4,553,545 | 11/1985 | Maass et al. . |
| 4,560,374 | 12/1985 | Hammerslag . |
| 4,572,186 | 2/1986 | Gould et al. . |

(List continued on next page.)

FOREIGN PATENT DOCUMENTS

| | | |
|---|---|---|
| 0364787A1 | 4/1990 | European Pat. Off. . |
| 0416662A2 | 3/1991 | European Pat. Off. . |
| 943788A1 | 12/1991 | European Pat. Off. . |
| 0505686A1 | 9/1992 | European Pat. Off. . |
| 3640745 | 6/1987 | Germany . |
| 57-89859 | 6/1982 | Japan . |
| 2135585 | 9/1984 | United Kingdom . |
| WO89/03232 | 4/1989 | WIPO . |
| WO90/01969 | 3/1990 | WIPO . |
| WO90/04982 | 5/1990 | WIPO . |
| WO90/06094 | 6/1990 | WIPO . |
| WO91/17744 | 11/1991 | WIPO . |
| WO92/10218 | 6/1992 | WIPO . |

OTHER PUBLICATIONS

Duprat, et al.: Flexible Balloon–Expanded Stent for Small Vessels, pp. 276–278, 1987, *Radiology Journal*.
Maas, et al.: Radiological Follow–Up of Transluminally Inserted Vascular Endoprostheses: An Experimental Study Using Expanding Spirals, pp. 659–663, 1984, *Radiology Journal*.
Palmaz, et al.: Expandable Intraluminal Graft: A Preliminary Study, pp. 73–77, 1985, *Radiology Journal*.
Wright, et al.: Percutaneous Endovascular Stents: An Experimental Evaluation, 69–72, 1985, *Radiology Journal*.
Dotter: Transluminal Expandable Nitinol Coil Stent Grafting: Preliminary Report, pp. 259–260, Apr. 1983.

*Primary Examiner*—Glenn Dawson
*Attorney, Agent, or Firm*—Fulwider Patton Lee & Utecht, LLP

[57] ABSTRACT

An intravascular stent including a cylindrical sheet having overlapping edges that interlock. The edges have a series of protrusions and apertures that interlock and ratchet as the stent expands to an open position to support a section of arterial wall. The stent may be expanded by a balloon catheter or it may be self-expanding. The stent is biocompatible, may be bio-erodible, and capable of localized drug delivery. A plurality of retaining members to keep the stent open are disclosed. In one embodiment a buckle fastening member is used, while in another embodiment a helical seam containing projections is employed. The stent may be wound in such a manner that during expansion of the stent one side of the sheet desires to return to its original shape, creating a bias. In addition, a variety of reticulated structure stents are disclosed, with novel geometric patterns that aid in increased flexibility while preserving radial strength and also allow blood-tissue interaction and side branch access. The intravascular stent may be made of a sheet of material strengthened and stiffened by pyrolytic carbon or by structural reinforcement as in composite laminates.

1 Claim, 11 Drawing Sheets

U.S. PATENT DOCUMENTS

| | | |
|---|---|---|
| 4,580,568 | 4/1986 | Gianturco . |
| 4,650,466 | 3/1987 | Luther . |
| 4,655,771 | 4/1987 | Wallsten . |
| 4,733,665 | 3/1988 | Palmaz . |
| 4,739,762 | 4/1988 | Palmaz . |
| 4,740,207 | 4/1988 | Kreamer . |
| 4,752,054 | 6/1988 | Jonsson . |
| 4,760,849 | 8/1988 | Kropf . |
| 4,776,337 | 10/1988 | Palmaz . |
| 4,788,751 | 12/1988 | Shely et al. . |
| 4,800,882 | 1/1989 | Gianturco . |
| 4,830,003 | 5/1989 | Wolff et al. . |
| 4,856,516 | 8/1989 | Beck et al. . |
| 4,878,906 | 11/1989 | Lindermann et al. . |
| 4,886,062 | 12/1989 | Wiktor . |
| 4,892,539 | 1/1990 | Koch . |
| 4,893,623 | 1/1990 | Rosenbluth . |
| 4,896,831 | 1/1991 | King et al. . |
| 4,907,336 | 3/1990 | Gianturco . |
| 4,913,141 | 4/1990 | Hillstead . |
| 4,922,905 | 5/1990 | Strecker . |
| 4,950,458 | 8/1990 | Savin et al. . |
| 4,969,890 | 11/1990 | Sugita et al. . |
| 4,990,155 | 2/1991 | Wilkoff . |
| 4,994,071 | 3/1991 | Macgregor . |
| 5,002,560 | 3/1991 | Machold . |
| 5,007,926 | 4/1991 | Deobyshire . |
| 5,015,253 | 5/1991 | MacGregor . |
| 5,019,085 | 5/1991 | Hillstead . |
| 5,019,090 | 5/1991 | Pinchuk . |
| 5,034,001 | 7/1991 | Garrison et al. . |
| 5,035,706 | 7/1991 | Giontureo et al. . |
| 5,037,392 | 8/1991 | Hillstead . |
| 5,041,126 | 8/1991 | Gianturco . |
| 5,059,211 | 10/1991 | Stack et al. . |
| 5,061,275 | 10/1991 | Wallsten et al. . |
| 5,064,435 | 11/1991 | Porter . |
| 5,071,407 | 12/1991 | Termin et al. . |
| 5,078,720 | 1/1992 | Burton et al. . |
| 5,078,726 | 1/1992 | Kreamer . |
| 5,078,736 | 1/1992 | Behl . |
| 5,084,065 | 1/1992 | Weldon et al. . |
| 5,100,429 | 3/1992 | Sinofsky et al. . |
| 5,104,404 | 4/1992 | Wolff . |
| 5,108,416 | 4/1992 | Ryan et al. . |
| 5,116,318 | 5/1992 | Hillstead . |
| 5,116,360 | 5/1992 | Pinchuk et al. . |
| 5,116,365 | 5/1992 | Hillstead . |
| 5,122,154 | 6/1992 | Rhodes . |
| 5,123,917 | 6/1992 | Lee . |
| 5,133,732 | 7/1992 | Wikter . |
| 5,135,536 | 8/1992 | Hillstead . |
| 5,158,548 | 10/1992 | Lau . |
| 5,161,547 | 11/1992 | Tower . |
| 5,163,951 | 11/1992 | Pinchuk et al. . |
| 5,163,958 | 11/1992 | Pinchuk . |
| 5,171,262 | 12/1992 | MacGregor . |
| 5,192,297 | 3/1993 | Hull . |
| 5,192,307 | 3/1993 | Wall ........................................ 606/198 |
| 5,192,311 | 3/1993 | King et al. . |
| 5,195,984 | 3/1993 | Schatz . |
| 5,197,978 | 3/1993 | Hess . |
| 5,290,295 | 3/1994 | Querals et al. . |
| 5,306,286 | 4/1994 | Stack et al. .............................. 606/198 |
| 5,423,885 | 6/1995 | Williams .................................. 623/12 |
| 5,443,500 | 8/1995 | Sigwart .................................... 606/192 |

RATCHETING STENT

This application is a division of U.S. Ser. No. 08/052,410, filed Apr. 23, 1993, now U.S. Pat. No. 5,441,515.

BACKGROUND OF THE INVENTION

1. Field Of The Invention

The present invention generally relates to expandable endoprosthesis devices, in particular expandable intraluminal vascular grafts, generally called stents, adapted to be implanted into a body lumen, such as a coronary artery, to maintain the patency of the lumen. These devices are frequently used in the treatment of atherosclerotic stenosis in blood vessels, especially after percutaneous transluminal coronary angioplasty (PTCA) procedures, with the intent to help reduce the likelihood of restenosis of a blood vessel. Stents are also used to support a body lumen where a flap or dissection has occurred or in general where the lumen is weak. The present invention also relates to an expandable intraluminal vascular graft that can be used in any body lumen.

2. Description Of Related Art

In expandable stents that are delivered with expandable catheters, such as balloon catheters, the stents are positioned over the balloon portion of the catheter and expanded from a reduced diameter to an enlarged diameter greater than or equal to the diameter of the artery wall, by inflating the balloon. Stents of this type can be expanded to an enlarged diameter by deforming the stent, by engagement of the stent walls with respect to one another, and by one-way engagement of the stent walls together with endothelial growth into the stent. Other stents are self-expanding, through the properties of the material constituting the stent or by design.

SUMMARY OF THE INVENTION

The present invention is directed to a stent, adapted to be inserted within a body lumen, and designed to expand and lock in an enlarged diameter form.

The stent of the present invention is designed to engage in a sure manner, and, once engaged, to stay engaged with a high degree of reliability.

The stent of the present invention comprises a variety of embodiments. In some embodiments of the stent the stent is locked along its seam by a locking member analogous to a "buckle." This buckle also may serve as a means for aligning the edges.

In another embodiment of the stent a helical seam employing teeth is used, so that failure of the stent along the locking portion will not result in catastrophic failure of the stent in maintaining patency. In yet another embodiment of the stent a plurality of reticulated structures are used to form the stent.

The stent of the present invention may be made of a variety of materials, including biocompatible and bio-resorbable (bio-erodible) polymers, thermal shaped memory polymers or metals, biocompatible metals, or super elastic materials such as nickel-titanium alloys. A material constituting the stent can be a thin flexible polymer material, such as a polyimide, coated with a thin strengthening material comprising a pyrolytic carbon.

The stent of the present invention is designed for flexibility coupled with radial strength.

The stent may be deployed in a body lumen through a variety of devices, including but not limited to balloon catheters and specialized stent delivery catheters.

3

Figure 27:
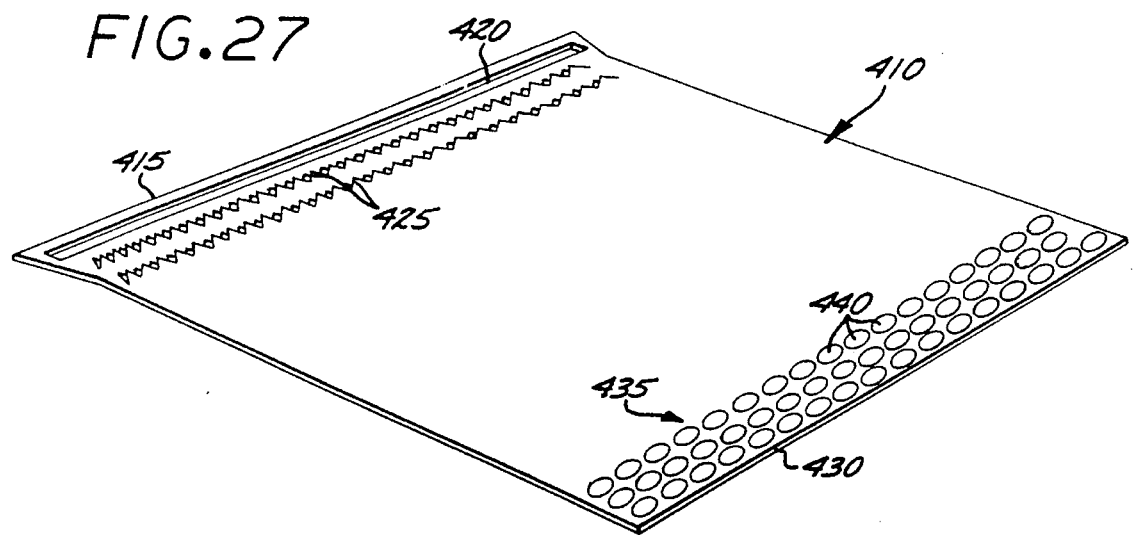

FIG. 27 shows a perspective view of a stent forming sheet of another embodiment of the present invention.

Figure 28:
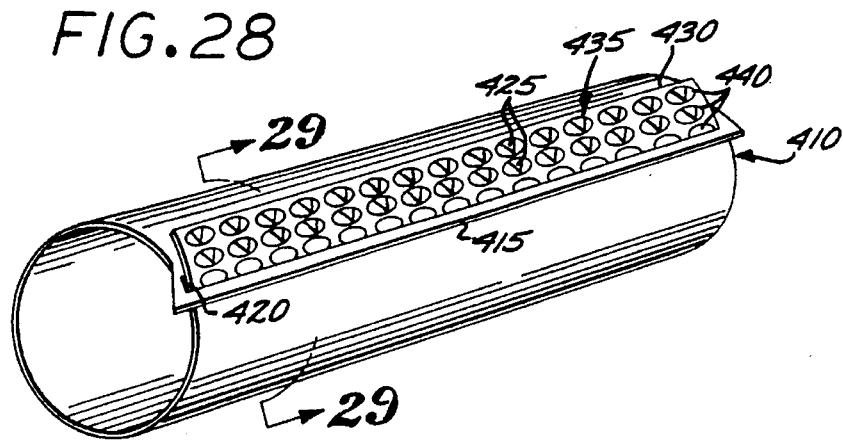

FIG. 28 shows a perspective view of a stent formed with the sheet of FIG. 27.

Figure 29:
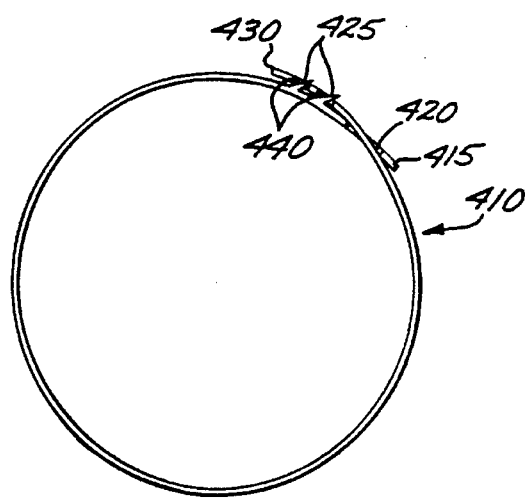

FIG. 29 shows a cross-sectional view of the stent of FIG. 28.

DETAILED DESCRIPTION

As shown by FIGS. 1–4, a flat sheet or membrane of material 10 is formed with an oval-shaped mesh pattern in the body portion 15 of the sheet. One end of body portion 15, buckle portion 20, includes a pair of rows of teeth 25 and an outer loop portion 30. The sheet is formed into a substantially cylindrically-shaped stent by passing the bottom end 35 through the outer loop portion 30 of buckle portion 20. Teeth 25 then engage oval-shaped apertures 33, which form a mesh pattern.

Figure 1:
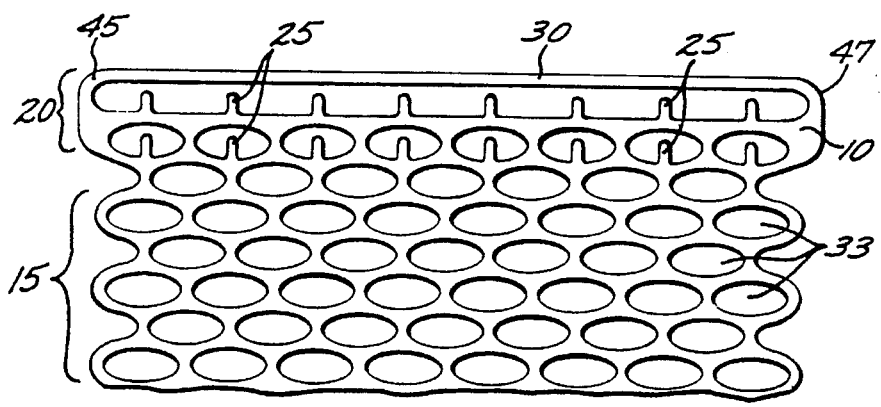
FIG. 1 shows a portion of a sheet forming the stent of one embodiment of the present invention.
Figure 2:
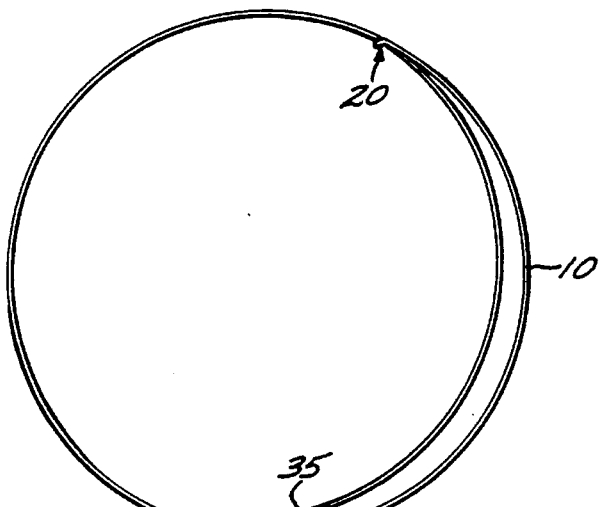
FIG. 2 shows a cross-sectional view taken along a plane perpendicular to the longitudinal axis of the stent of FIG. 1, when the stent is rolled up in a reduced diameter form.
Figure 3:
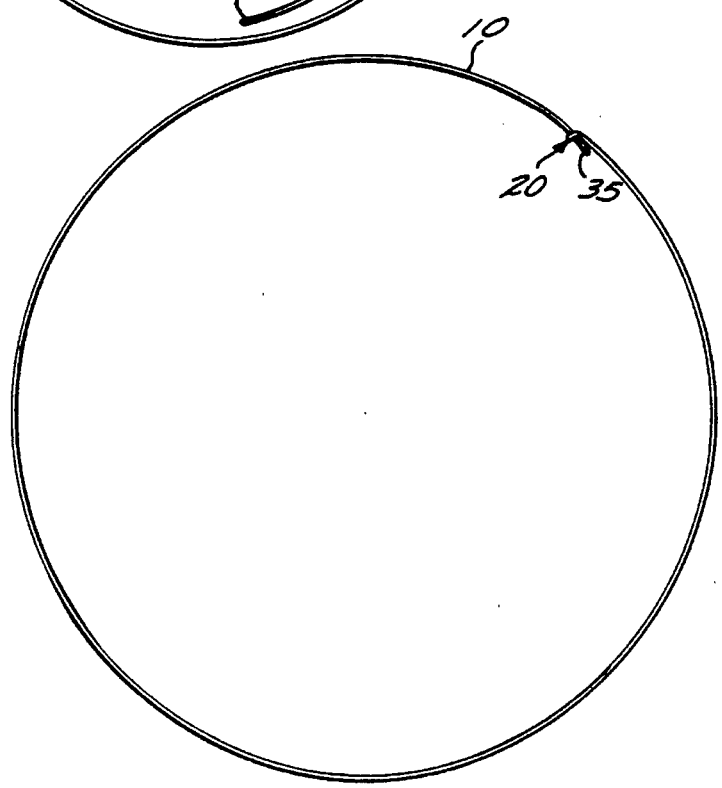
FIG. 3 shows a cross-sectional view taken along a plane perpendicular to the longitudinal axis of the stent, when the stent is unrolled in an expanded diameter form.
Figure 4:
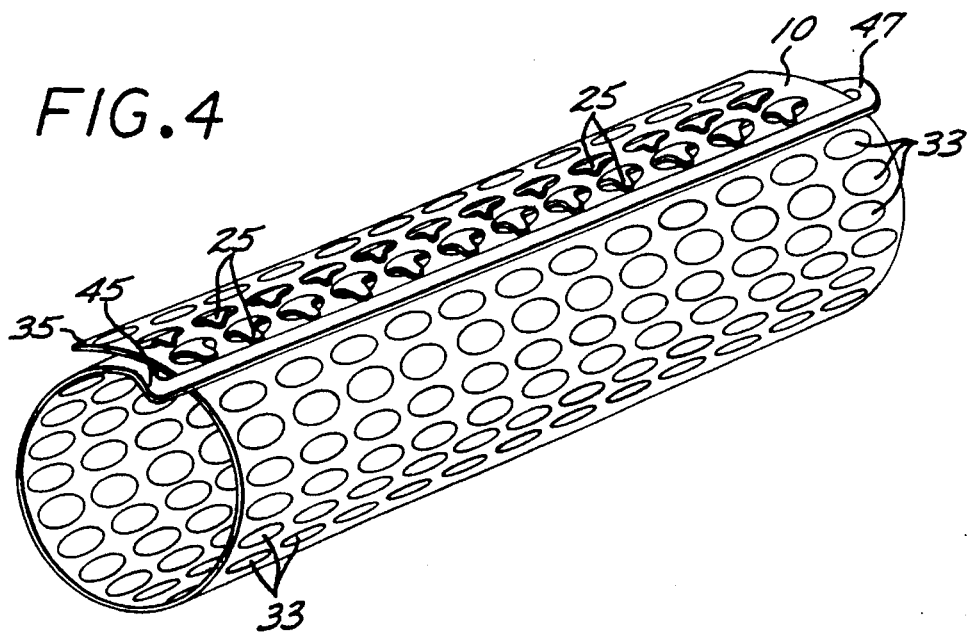
FIG. 4 shows a perspective view of an embodiment of the present invention.

As seen in FIGS. 2, 3 and 4, the bottom end 35 is threaded through buckle portion 20, which forms a loop or slot extending along the longitudinal axis of the stent, and has loop ends 45, 47. In FIG. 2 the stent is shown in a reduced diameter form, and in this form the stent is placed on a stent delivery catheter to be transported to a site in a vessel at which the stent is to be deployed. The stent is then expanded to an enlarged diameter form for deployment, as shown in FIG. 3.

Operation of the stent of the present invention will now be described. The stent of the present invention is placed over a stent delivery catheter that has been prepared for PTCA angioplasty. The catheter is percutaneously introduced into a vessel, following a previously positioned guidewire in an over-the-wire angioplasty catheter system, and tracked by a fluoroscope, until the balloon portion and associated stent are positioned at the point where the stent is to be placed. The balloon is then inflated and the stent is expanded by the balloon portion from a reduced diameter form to an expanded diameter form. After the stent has been expanded to its final expanded diameter, the balloon is deflated and the catheter is withdrawn, leaving the stent in place. As is appreciated by those skilled in the art, the stent while being transported is of a sufficiently small, reduced diameter as to allow it to be readily transported through a vessel. Buckle portion 20 keeps the rows of teeth 25 engaged with apertures 33, at a suitable angle of engagement, to help prevent misalignment and incorrect engagement.

Figure 5:
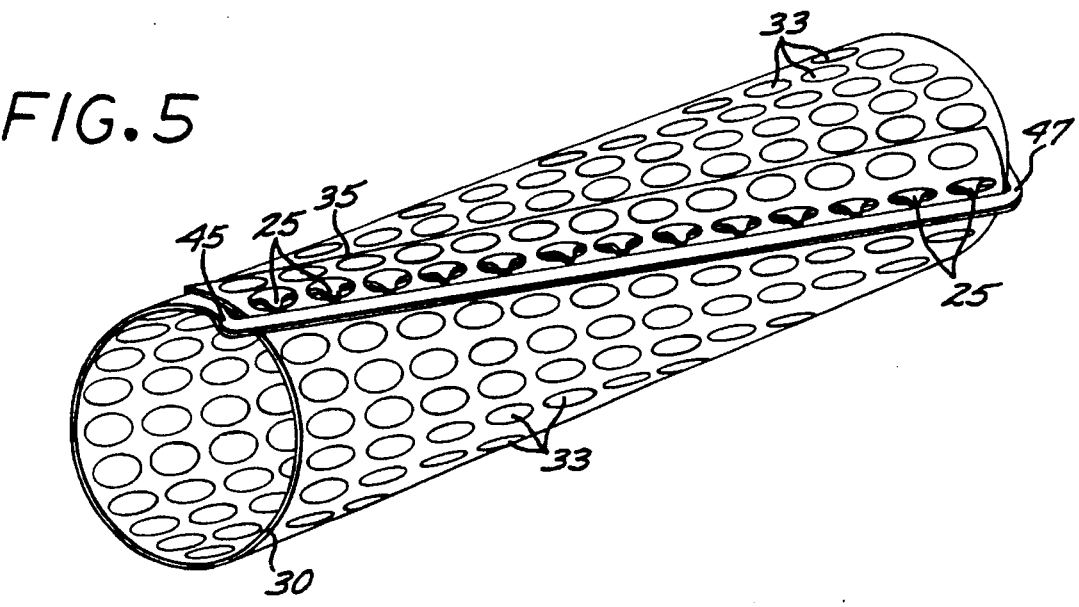
FIG. 5 shows a perspective view of another embodiment of the present invention, showing the locking seam offset along a helical spiral.

FIG. 4 shows a perspective view of this locking feature of this embodiment of the present invention, while FIG. 5 shows a perspective view of a substantially parallelogram-disposed sheet forming this embodiment of stent, employing a helically-extending slot buckle. The helically-extending slot insures that the stress loads are directed in a direction anti-parallel to the longitudinal axis of the stent, which helps prevent catastrophic failure.

A material constituting any embodiment of stent can be a thin flexible polymer material, such as a polyimide, coated with a strengthening material comprising a pyrolytic carbon. The pyrolytic carbon coating is preferably only about one angstrom ($10^{-10}$ m) thick, which does not increase the cross-sectional profile of the stent in any appreciable manner, yet provides for increased tensile strength, stiffness, and resistance to radial compression. Furthermore, the pyrolytic carbon layer is anti-thrombogenic. This material can not only be employed in the stent embodiment shown in FIGS. 1–4, but also may be employed in all embodiments of stents disclosed herein. Furthermore, in all of the embodiments of stents disclosed herein the material comprising the stent may be made of a biodegradable material, and may be a material impregnated with a drug, so the stent may locally treat a particular lesion or disease.

Expansion of stent 10 from a reduced diameter form into an expanded diameter form is preferably performed by a balloon catheter. Any other means for expanding the stent, however, may be used. Furthermore, the present stent is not limited to use in coronary arteries and over-the-wire angioplasty catheter systems, but the stent may be deployed in any body lumen by any suitable means.

Another feature of the present invention of FIGS. 1–4 is the spiral shape assumed by the cross-section of the stent when it is rolled up in a reduced diameter form as shown in FIG. 2. When the stent is expanded from a reduced diameter form, as shown in FIG. 2, to an expanded diameter form, as shown by FIG. 3, end 35 is deflected by a greater angle of rotation and/or translation than the buckle end 20, due to the geometry and composition of the wound up stent. This results in end 35 undergoing more deformation than end 20. Consequently end 35, and the bottom portion of the body portion 15, desires to return to its original reduced diameter shape more readily than buckle end 20 and the top buckle portion of body 15, which makes the stent resiliently biased radially inward. The stent thus is biased to return to its reduced diameter form. This resiliency helps teeth 25 engage apertures 33 more completely. The bias feature can be built into all suitable embodiments of the present invention.

Figure 6:
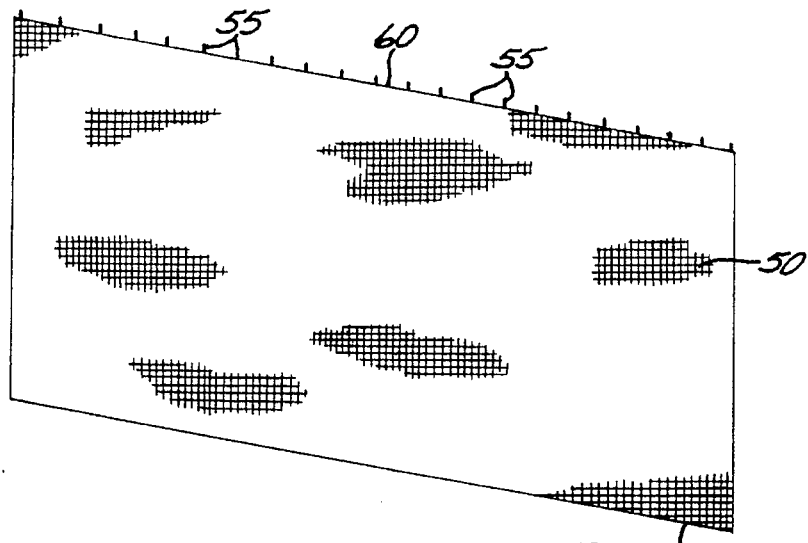
FIG. 6 shows another embodiment of the present invention, showing a sheet forming the stent, prior to being rolled up to form the stent.
Figure 7:
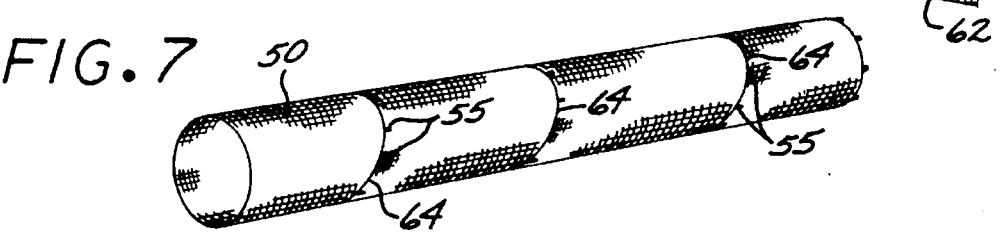
FIG. 7 shows a perspective view of a stent formed by the sheet of FIG. 6 of the present invention.

Turning attention now to the embodiment of FIGS. 6 and 7, there is shown a sheet of material 50, in substantially the shape of an elongated parallelogram, having sides 60, 62, with side 60 having a plurality of projections 55 extending from the side. Sheet 50 may be formed of any suitable material, and may be woven, textured or contain apertures like the embodiment of FIG. 1. Sheet 50 is wound into an elongated cylinder, with the sides 60, 62 overlapping and forming a helical seam 64 spiralling about the longitudinal axis of the stent. Projections 55 engage the material and maintain the stent in an enlarged diameter form, when the stent is expanded in the manner described above.

Figure 8:
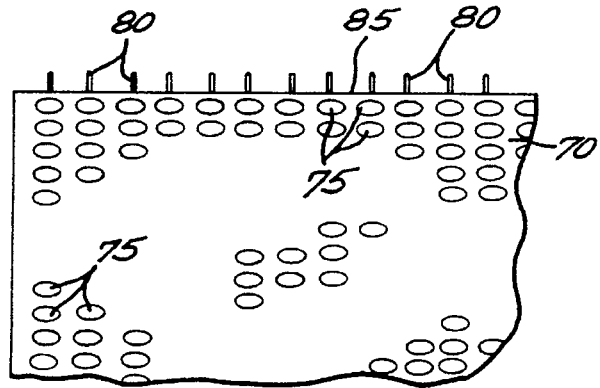
FIG. 8 shows an embodiment of the present invention showing a portion of a stent forming sheet having apertures and projections.
Figure 9:
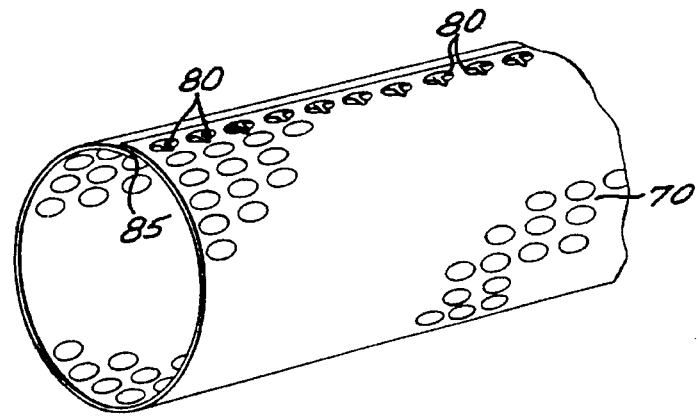
FIG. 9 shows a perspective view of a stent formed by the sheet of FIG. 8 of the present invention.

FIG. 8 shows another embodiment of the present invention. A substantially rectangular sheet 70 is formed with a plurality of apertures 75. On longitudinal edge 85 there are a plurality of projections 80 that engage apertures 75 when the stent is rolled up. As shown in FIG. 9, when the sheet is rolled up into a cylindrical stent, the edges of the sheet overlap along the longitudinal axis of the stent and projections 80 engage apertures 75 to lock the stent in an expanded diameter form, to resist collapse of the stent back into a reduced diameter form. The stent may be made of the same material as the embodiment of FIG. 1.

Figure 10:
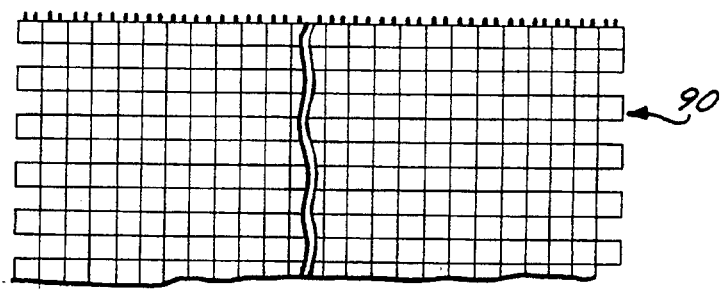
FIG. 10 shows an embodiment of stent forming sheet employing a reticulated box-like configuration.
Figure 11:
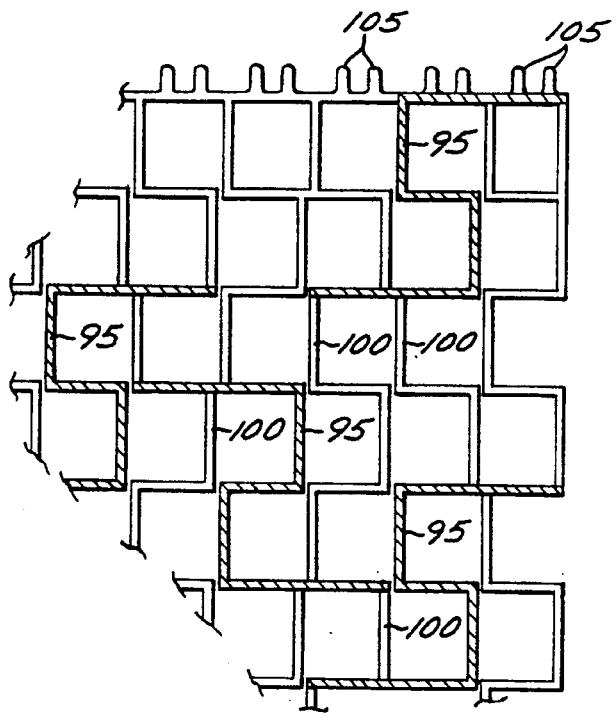
FIG. 11 shows a closeup view of a sheet employing reticulated S-shaped members.

Turning attention now to FIG. 10, there is shown another embodiment of the present invention. A sheet of material 90 constituting the stent is made up of a reticulated structure having protrusions 91 on one longitudinal edge which will engage the reticles on the opposite longitudinal edge when the stent is expanded from its reduced diameter state upon deployment in the body lumen to lock the stent in its expanded configuration. In FIG. 11, the reticulated structure employs S-shaped bars 95 that are linked with one another by interspaced linking bars 100 at the top and bottom portions of the S-shaped bars. At the edge of sheet 90 is a row of teeth 105 that form locking projections to engage the apertures in sheet 90 when the sheet is rolled into a cylindrical shape to form the stent. As can be seen from FIG. 11, the placement of the linking bars 100 along the S-shaped bars 95 and the spacing of the S-shaped bars 95 about one another may be a repeating pattern, such as a pattern that achieves a substantially spiral pattern of S-shaped bars about the stent longitudinal axis, insuring flexibility. The reticulated structure shown may be employed in all embodiments of the present invention.

Figure 12:
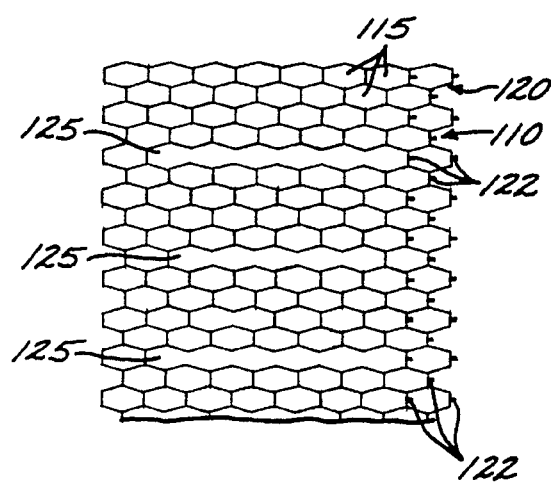
FIG. 12 shows an embodiment of the present invention using a reticulated honeycomb-like structured sheet material having horizontally spaced gaps to allow increased flexibility.
Figure 13:
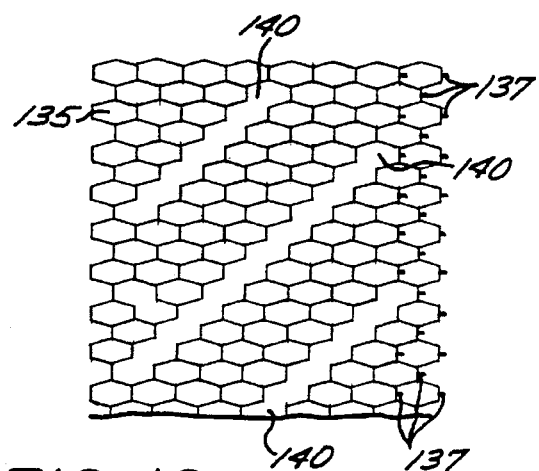
FIG. 13 shows an embodiment of the present invention using a reticulated honeycomb-like structured material having transversely spaced gaps to allow increased flexibility.

Turning attention to FIGS. 12 and 13, there are shown alternate embodiments of the present invention disclosing reticulated structures having honeycomb-like cells with gaps interrupting the honeycomb-like cells in the reticulated structures to increase flexibility. In FIG. 12, sheet 110 has a plurality of honeycomb-like cells 115 that end at edge 120 in a row of locking teeth 122, which function as in the above embodiments to hold the stent open in an enlarged diameter form. In addition, horizontally spaced gaps 125 among the honeycomb cells 115 allow increased flexibility when sheet 110 is rolled up into a cylindrical form with overlapping edges extending along a longitudinal direction. The gaps 125 extend along the horizontal direction orthogonal to the longitudinal direction of the sheet, which extends along the longitudinal axis of the stent. When the stent is formed from the honeycomb-like sheet, gaps 125 form a series of bars interspaced along the longitudinal axis. Likewise as shown in FIG. 13, sheet 130 has a plurality of honeycomb like cells 135 that end at the edge in two rows of locking teeth 137, with the addition of diagonally slanted gaps 140 to allow increased flexibility. The diagonally slanted gaps 140 form a spiral configuration along the longitudinal axis of the stent.

Figure 14:
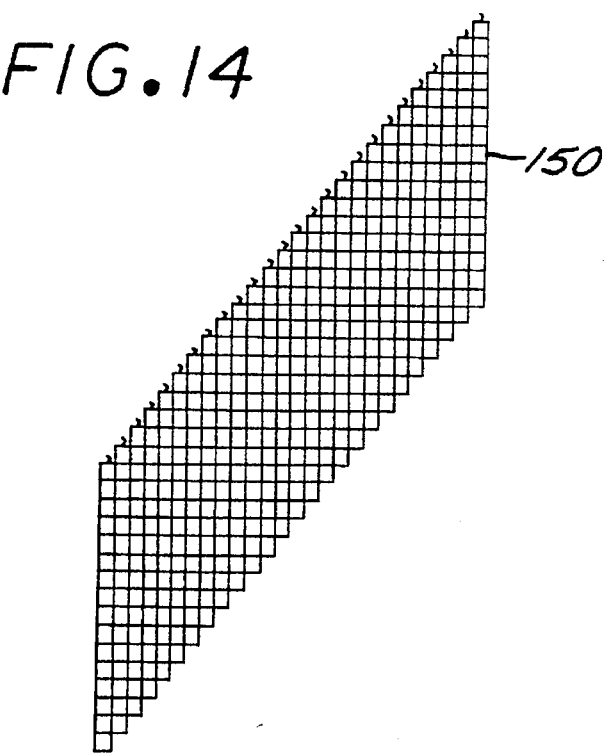
FIG. 14 shows an embodiment of the present invention using a parallelogram shaped reticulated structured stent forming material having a helical locking seam with a plurality of hook shaped members on the helical seam.
Figure 15:
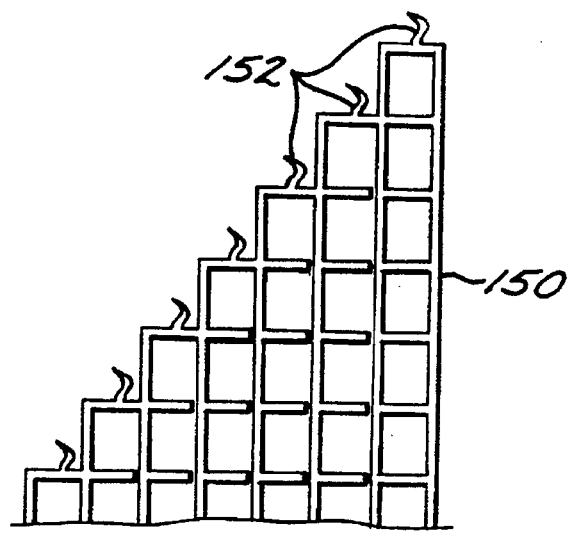
FIG. 15 shows an enlarged portion of the sheet of FIG. 14.

Turning attention to FIGS. 14–15 there is shown another embodiment of the present invention. A parallelogram-shaped reticulated sheet 150 is made up of box shaped cells that end along one edge in a series of locking members, hooks 152. The sheet 150 is rolled into a cylindrical form, as in the embodiment shown in FIG. 7. Like the embodiments of FIGS. 5 and 7, one advantage of a helically extending longitudinal seam over a non-helically extending longitudinal seam is that in the event of a failure, a break or tear between the locking members and the sheet will not propagate along the longitudinal direction in as ready a manner as when the load is distributed over a non-helical interface. In addition, the helical locking seam appears to distribute the load along the locking member interface in a more stable manner than a non-helical locking seam.

Figure 16:
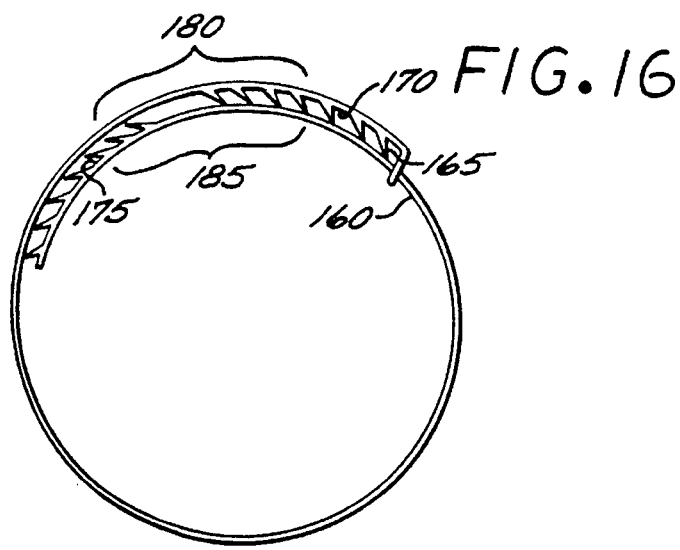
FIG. 16 shows a cross-sectional view of an embodiment of the present invention employing overlapping edges engaged by teeth.

As shown by FIG. 16, a sheet or membrane of material 160, which may be any material suitable for a vascular prosthesis or stent, is formed with protrusions or teeth 165 on both sides of the edges of the sheet. As the sheet is rolled up to a cylindrical shape the upper edge 170 will become the outer surface 170 of the cylindrical stent and the lower edge 175 will become the inner surface 175 of the stent.

The protrusions are in the form of rows of individual teeth. In general the protrusions may be formed in any shape and in any manner, including but not limited to machining, etching, thermo-curing process, injection molding, laser machining, extruding, casting and adding the protrusions to a smooth body made of the same or different material from the protrusions, or treating the body to create a roughened surface texture. In one embodiment, the teeth are arranged in a substantially orderly, spaced arrangement of rows. In addition, the stent may be made directly into a cylindrical shape without first forming a flat sheet.

As can be seen from FIG. 16, the stent is formed from a rolled-up cylinder of material having overlapping edges 180, 185, which lie along the longitudinal axis of the cylinder in a substantially parallel manner. Edge 185 fits through buckle slot 210, which serves as both a locking component and an alignment component. Teeth 165 on each overlapping edge are slanted or sloped in opposite directions to each other, to form a one-way locking arrangement that resists collapse of the stent to a smaller diameter, once the teeth are engaged. The stent is configured so it inherently tends to roll up into a smaller diameter, but is prevented from doing so by the interlocking teeth.

When the teeth are engaged to one another the slope of the teeth allows the stent to be unrolled to an enlarged diameter much more readily than the stent can be collapsed to a rolled-up, reduced diameter. The cooperation of the teeth lock the stent in an expanded diameter form.

Operation of the stent of the present invention will now be described. The stent is expanded from a reduced diameter, which is the state the stent is in while it is being transported through the vasculature, to an expanded diameter, which is the state the stent is in when operationally deployed in the vasculature. As is appreciated by those skilled in the art, the stent while being transported is of a small, reduced diameter sufficient to allow it to be readily transported through a body lumen. In this reduced diameter form the stent would be a rolled cylindrical sheet with overlapping edges, but teeth 165 would not be in contact with each other. When the stent is expanded from its reduced diameter to its enlarged diameter, the teeth would engage each other and the stent would be locked in an operational manner to function as a prosthesis.

Expansion of the stent from a reduced diameter into an expanded diameter is preferably performed by a balloon catheter or other mechanical means. Any other means for expanding the stent, however, may be used, including relying on the expansive properties of the material of the stent itself, which may be made of a shape memory material such as a polymeric compound including a nickel-titanium (NiTi) alloy, for example, those compounds manufactured under the trademarks NITINOL and ELASTINITE, or other super elastic materials. Furthermore, it should be understood that the present stent is not limited to use in coronary arteries and angioplasty catheter systems, but the stent may be deployed in any body lumen by any suitable Briefly and in general terms regarding the use of a balloon catheter to deploy the stent, when the stent is to be deployed in a coronary artery, the stent is placed over and mounted on the balloon portion of a catheter that has been prepared for PTCA. The catheter is percutaneously introduced into a body lumen, following a previously positioned guidewire in an over-the-wire angioplasty catheter system, and tracked by a fluoroscope, until the balloon portion and associated stent are positioned at the point where the stent is to be placed. Thereafter the balloon is inflated and the stent is expanded by the balloon portion from a reduced diameter to an expanded diameter. After the stent has been expanded to its final expanded diameter, the balloon is deflated and the catheter is withdrawn, leaving the stent in place.

Deployment of the stent made of a super elastic material could be achieved by confining the stent to a minimum diameter, for example by enclosing the stent while in its reduced diameter with a sheath, and allowing the stent to expand when it is desired to employ the stent in an operational, expanded diameter form, by retracting the sheath. In this case the expansion of the stent occurs due to the inherent properties of the material constituting the stent. The properties of these super elastic materials are known by those skilled in the art.

Similarly, thermal shape memory polymers or metallic materials may be used as a stent material for another similar kind of self-expanding stent. These thermal memory stents have a transition temperature set at such a value that at a normal body temperature the stent is in a collapsed (plastically deformed) state, but with the application of heat, such as via a hot balloon catheter or a hot liquid (such as saline) perfusion system, the stent would expand by itself to assume its final diameter in the body lumen.

Stainless steel, tantalum, gold, platinum or another biocompatible metal, such as suitable tungsten alloys, also may be used as a material for the stent of the present invention.

The stent may be made of a bioabsorbable material, allowing the stent to dissolve. Such materials include, but are not limited to, polymers of the linear aliphatic polyester and glycolide families. The stent may also be made of a material having a lubricous coating such as silicone so that it has less resistance during deployment. These materials may also contain or be impregnated with various drugs, so that the stent may be used as a localized drug delivery device. The drugs impregnating the stent may include enzymes to prevent blood coagulation, or medication to prevent hyperplastic response from a blood vessel or body passageway or reduce the likelihood of restenosis.

Other materials contemplated for the stent embodiments of the present invention include biocompatible polymers, such as of the type from the polyethylene, polyester and polypropylene families and plastics such as a polymer from the linear aliphatic polyester family, such as poly(lactic acid), poly(glycolic acid) or polycaprolactone, and their associated copolymers, degradable polymers such as polyorthoester, polyanhydride, polydioxanone and polyhydroxybutyrate.

Figure 17:
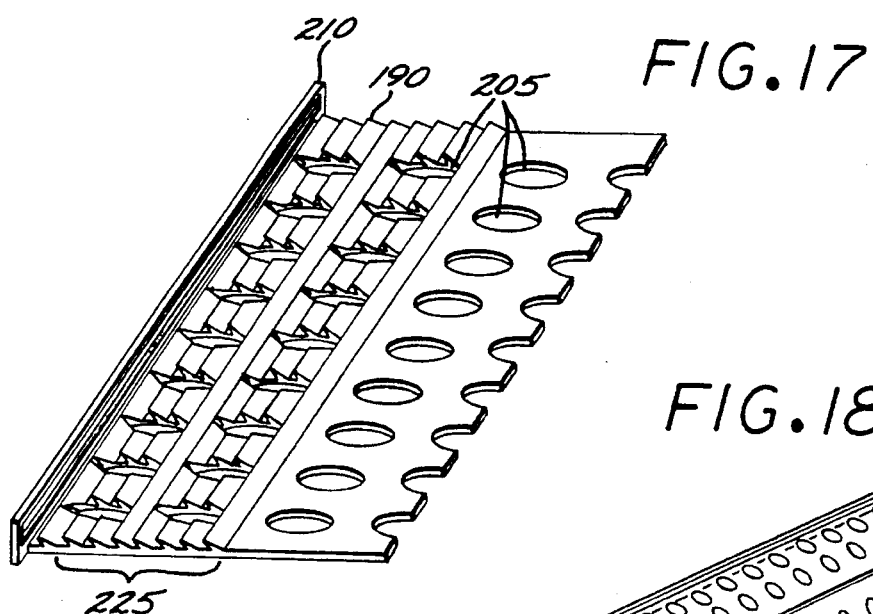
FIG. 17 shows an enlarged view of the edge of a stent portion.

Turning now to FIG. 17, there is shown a protrusion pattern for the longitudinal edge of the stent of the present invention. A stent made according to the FIG. 17 embodiment has its teeth formed of triangular ridges 190, formed to extend along longitudinal rows extending along the length of the stent, to form a serrated longitudinal edge 225. Both the inner and outer sides of the cylindrical sheet forming the stent have such serrated edges.

Figure 18:
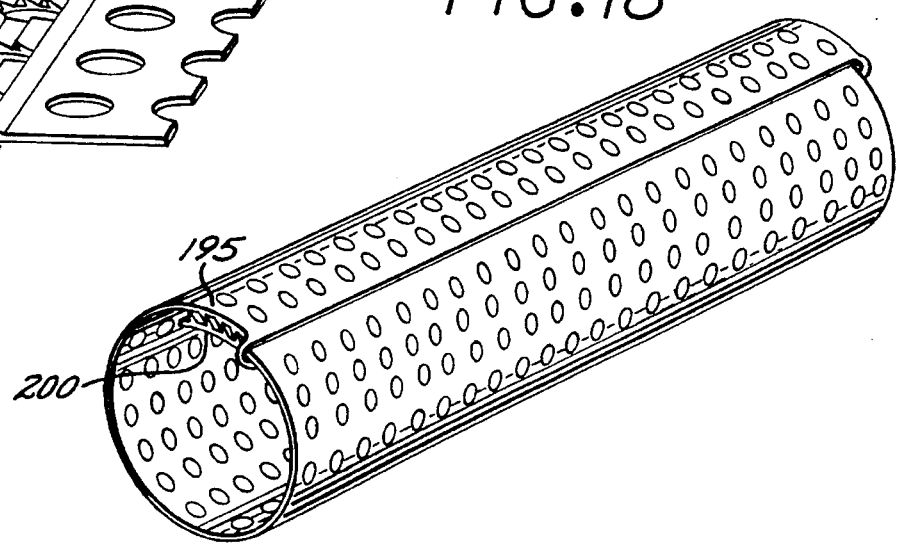
FIG. 18 shows a perspective view of a stent of the FIG. 17 embodiment.

Thus, as shown in FIG. 18, the triangular ridges lying on the inner surface of the stent would protrude radially inwardly toward the center of the cylindrical stent, and would lie on the outermost, overlapping, longitudinal edge 195 of the stent, the edge overlying innermost longitudinal edge 200. Likewise the triangular ridges that lie on the outer surface of the stent would protrude radially outwardly away from the of the cylindrical stent. As before, the triangular ridges on both the innermost and the outermost longitudinal edges are sloped to resist collapse of the stent to a reduced diameter after it has been expanded to its larger diameter.

In addition, there exist apertures 205 in the stent to allow endothelial growth into the stent, blood tissue inter-action, access for side-branch patency, and as an aid for mechanical flexibility. The stent can have more or fewer apertures than depicted, or none at all, depending upon the desired application.

Figure 19:
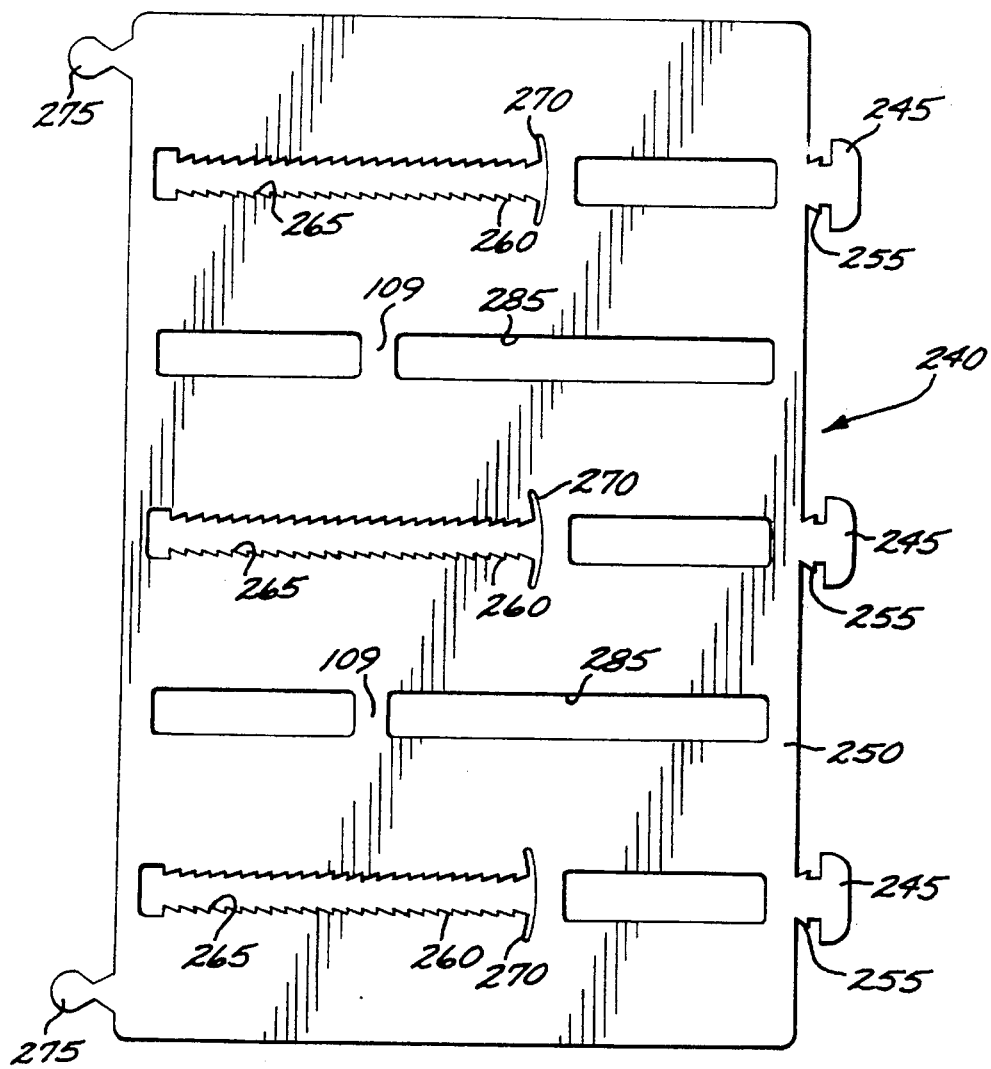
FIG. 19 shows a view of a stent forming sheet of material employing locking tabs.
Figure 20:
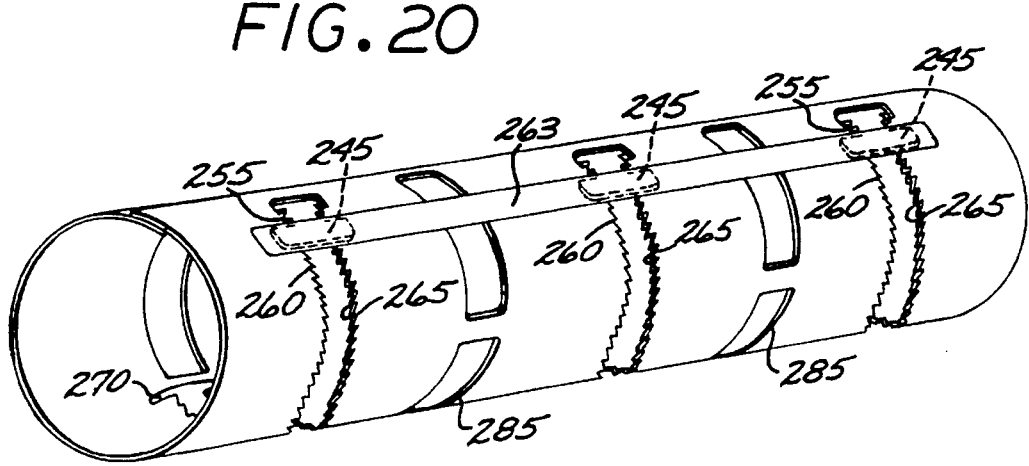
FIG. 20 shows a perspective view of an embodiment of the present invention formed from the sheet of FIG. 19.

Yet another embodiment of the invention is depicted in FIGS. 19 and 20. An intraluminal stent 240 has a plurality of tabs 245 along edge 250 of the stent. Each of tabs 245 has a plurality of teeth 255 adapted to engage teeth 260, which are located along the edges of elongated slots 265.

Each of tabs 245 and elongated slots 265 are aligned on the stent so that tab 245 can be inserted in crescent-shape aperture 270 of the slot. When the tab is properly positioned in the elongated slot, the teeth 255 on the tabs engage and interlock with the teeth on elongated slot 265, thereby locking the stent in a cylindrical form at a specific yet easily adjustable diameter. In order to prevent tabs 245 from unintentionally disengaging, a reinforcing member 263 may be affixed to all of the tabs after the stent is rolled. Furthermore, a pair of breakaway tabs 275 may be used to connect the sheet at its overlapping edges while the stent is being transported, to maintain the stent in a reduced diameter form and preserve a minimal profile during transport of the stent through a vasculature. Such breakaway tabs may be employed in all embodiments of stents of the present invention.

The deployment of stent 240 in a patient is much the same as previously described. The intraluminal stent is collapsed to a first diameter onto the balloon portion of a balloon catheter and delivered to the site of deployment in the manner previously described.

When the balloon portion of the catheter is inflated, stent 240 will correspondingly expand radially outwardly until it comes in contact with that portion of the body lumen where it is to be deployed. As the stent 240 radially expands, retaining tabs 275 will break away and permit the stent to expand proportionately. The teeth 255 on tabs 245 will ratchet along teeth 260 of elongated slots 265 and will engage in an inter-locking manner once expansion is completed. The inherent tendency of the intraluminal stent to close, as well as any force exerted by the walls of the body lumen on the outside of the stent, are sufficient to maintain teeth 255 and teeth 260 in an interlocking relationship so that the intraluminal stent maintains its form as cylindrical body 280.

Intraluminal stent 240 may have a plurality of elongated apertures 285 which have hereinbefore been described to allow endothelial growth into the stent, blood tissue interaction, access from side-branch patency, and to provide for mechanical flexibility. If the stent is positioned in a particularly tortuous vessel or in a curved area, it is desirable that the stent be able to flex somewhat along its longitudinal length so that the ends of the stent do not irritate the vessel wall. Flexibility is also desirable for stent deliverability. Elongated apertures 285 facilitate the flexibility of the stent in curved areas. Apertures 285 may take many geometric shapes and still accomplish the desired objectives. For example, the apertures may be a plurality of randomly spaced laser pinholes throughout the stent.

Figure 21:
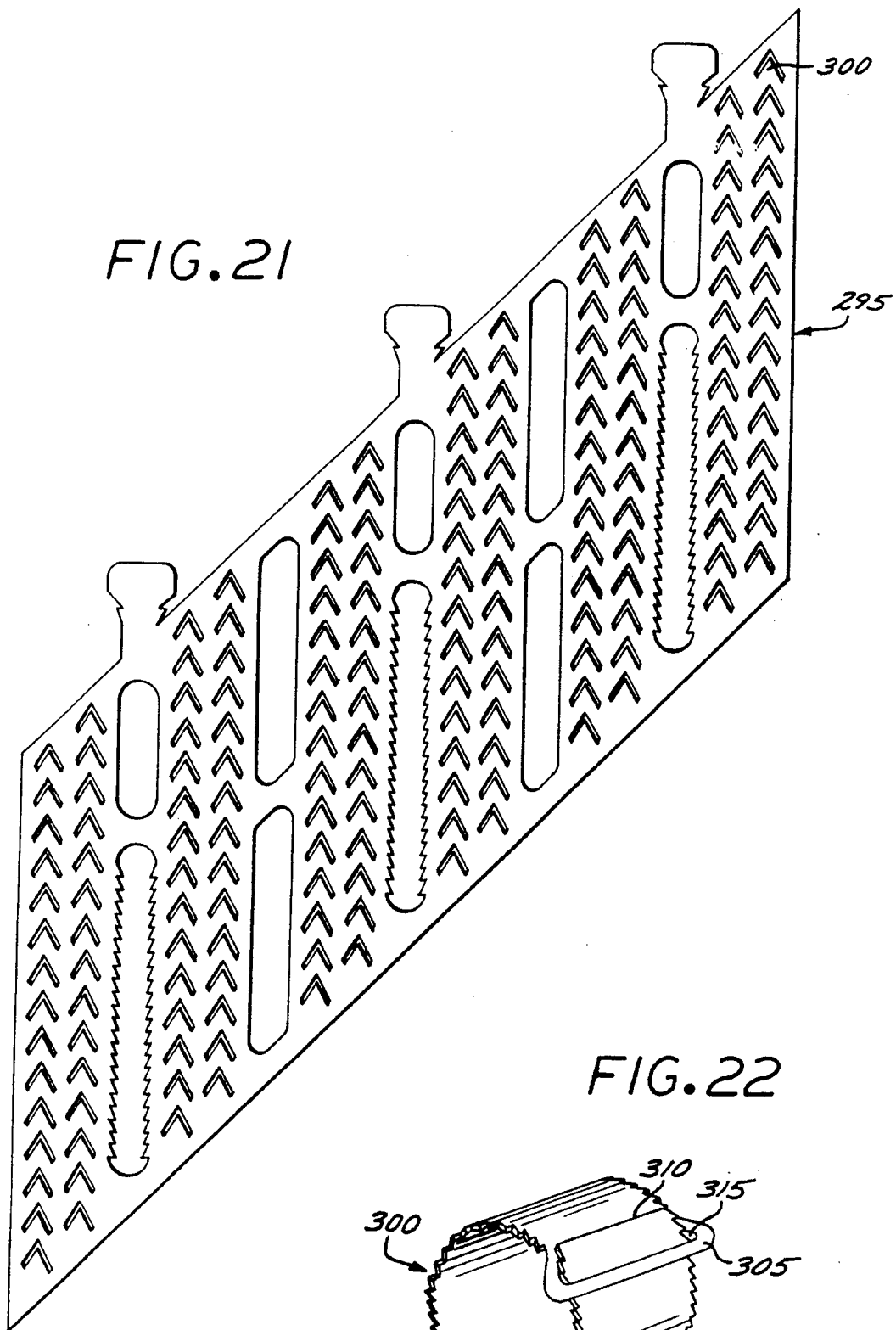
FIG. 21 shows a view of a stent forming sheet of material employing a parallelogram shape.

FIG. 21 discloses another embodiment of stent that employs a parallelogram shape, and uses triangular notches as apertures to both grip the stent and encourage endothelium growth. In this embodiment the stent would have a helically-spiralling seam, by nature of its parallelogram shape.

As previously stated with respect to other embodiments, the intraluminal stent can be made of plastics, metals, and super elastic materials as described. Further, the intraluminal stent can be impregnated with various drugs, may be biocompatible and/or bio-erodible.

In another embodiment of the invention, the stent can be in the form of one or more rings rather than a cylinder. It is contemplated that a plurality of rings could operate either independently of one another, either singularly or plurality in a side by side fashion, or, the rings could be interconnected to one another.

Figure 22:
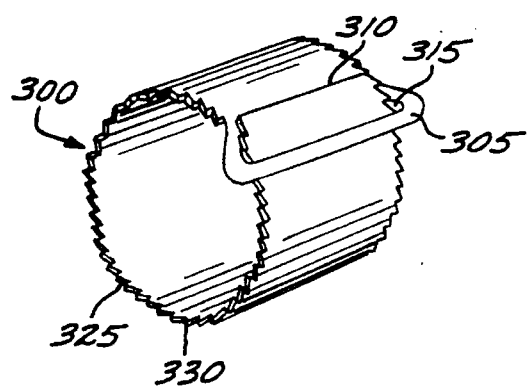
FIG. 22 shows a perspective view of another stent, employing a ring-like configuration.

For example, as shown in FIG. 22, an embodiment of the present invention depicts stent 300 having a first longitudinal edge 305 and a second longitudinal edge 310. First longitudinal edge 305 comprises an elongated slot 315 that is slightly wider than the width of second longitudinal edge 310. A plurality of teeth or protrusions 325 extend substantially the entire length 330 of the stent ring. There may be fewer teeth than is depicted in FIG. 22, depending upon the use of the stent and the nature of the body lumen in which it will be deployed. Tooth geometry may vary widely.

Stent 300 is coiled or rolled-up into a cylindrical configuration by inserting second longitudinal edge 310 through elongated slot 315 and sliding the stent onto the balloon portion of a catheter so that it has a low profile for transport through a body lumen. When the stent is positioned at the location where it is to be deployed, the balloon portion of the catheter is expanded, as previously described with other embodiments, until the stent comes in contact with the arterial wall. As the stent expands to its larger diameter, teeth 325 engage the edges of slot 315, in a ratcheting manner, until the stent is fully expanded. As previously described, the stent has a tendency to return to its coiled configuration and is prevented from doing so by the interlocking relationship between teeth 325 and slot 315. As can be appreciated, the geometric shape of that portion of the stent surrounding elongated slot 315 may take any shape. Further, the dimensions of the stent can vary depending upon the application. As also can be appreciated, but not shown in the drawing figures, stent 300 may have a plurality of apertures that would increase its flexibility so it could be placed in a tortuous area of a coronary artery.

Figure 23:
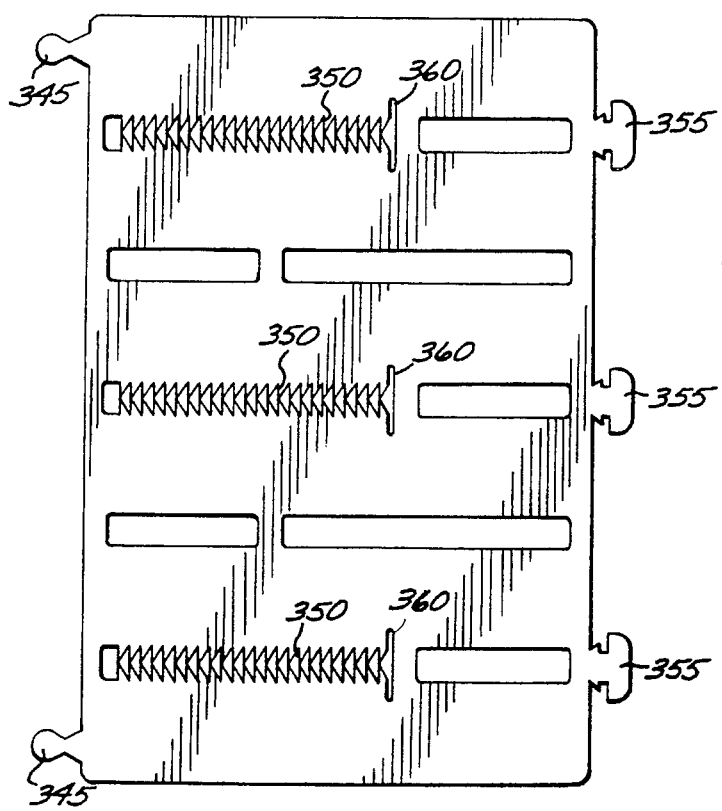
FIGS. 23–26 show laid out views of other embodiments of stent forming sheets.
Figure 24:
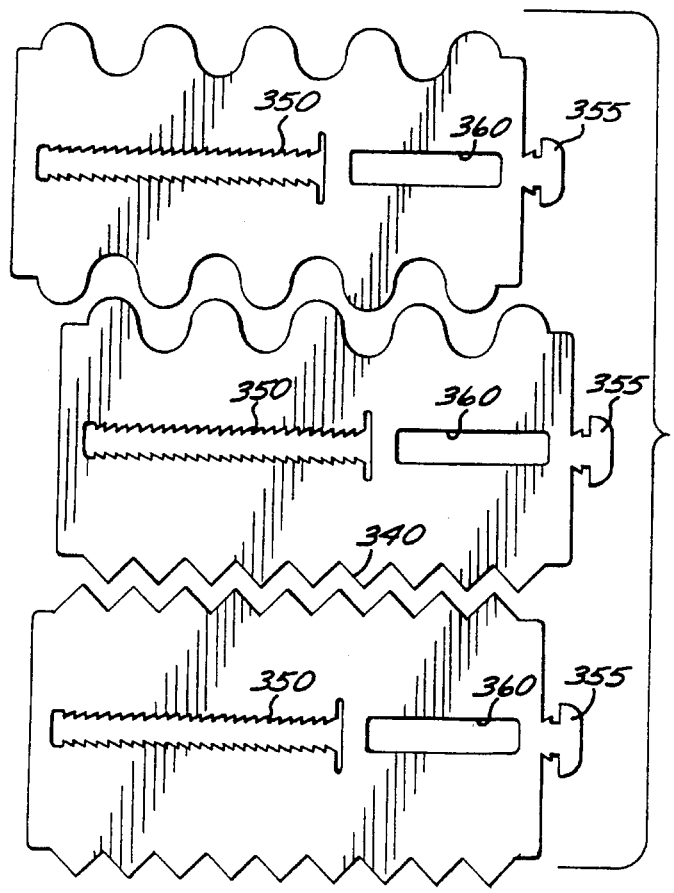

Other embodiments of sheets forming ring stents are shown in FIGS. 23 and 24. As can be seen from the figures, the ring stents are either interconnected (FIG. 23) or spaced from one another in a zig-zag or sinusoidal fashion (FIG. 24). If the ring stents are spaced from one another, as in FIG. 24, the edges 340 may be tapered, so that if the rings stents overlap the profile may be kept at a minimum. It should be noted that the stent of FIG. 23, as any of the stent embodiments of the present invention, may employ a breakaway tab 345 to maintain the stent in a reduced diameter form during transport of the stent through a vasculature, with the tab breaking when the stent is expanded during deployment. In addition, the stent of FIG. 23 may have teeth 350 joined together in a unitary construction, for better structural integrity, with the teeth breaking apart when tab 355 is inserted into slot 360 and the stent expanded.

Figure 25:
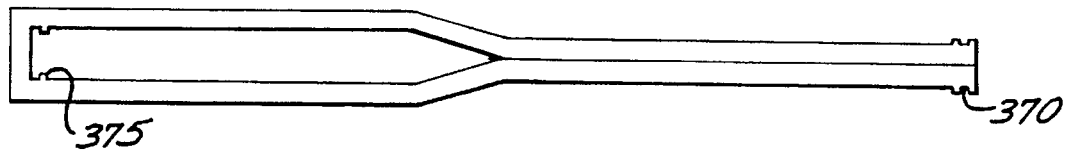

Another embodiment of stent employing a single stent ring is shown in FIG. 25. Here one or more teeth 370 engages one or more protrusions 375 inside of a slot-like portion of the stent.

Figure 26:
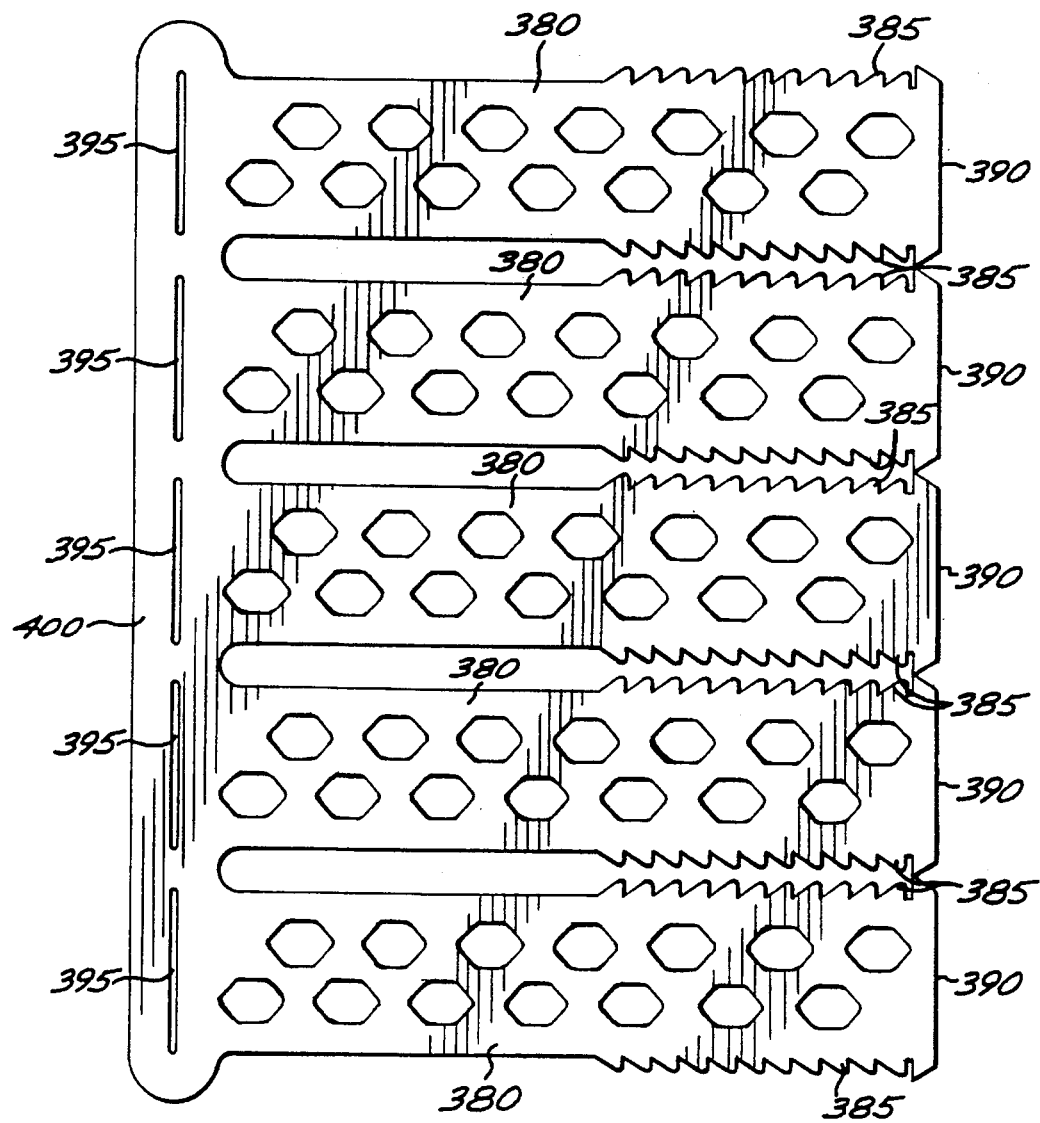

Yet another example of a stent employing a plurality of rings is depicted in FIG. 26. A plurality of strips or stent rings 380 are formed from a sheet of material, with the stent rings 380 having along their edges teeth 385. The stent rings are formed by passing ends 390 through slots 395, whereupon the stent is formed into a cylindrical shape having a plurality of stent rings joined at tab portion 400. The stent so formed is able to be expanded to a plurality of different size diameters along its axial length, because the stent rings 380 can be expanded to various diameters independent of one another, as they are joined only a connecting tab portion 400. The stent thus formed may be made more flexible. Furthermore, breakaway tabs may be employed to keep the stent in a collapsed state until such time that the stent is to be deployed, at which time the stent may be expanded and the breakaway tabs broken.

In another embodiment of the invention, depicted in FIGS. 27–29, an intraluminal stent 410 is depicted as a flat sheet and in its rolled-up cylindrical configuration. A first longitudinal edge 415 has a slot 420 adjacent the edge and extending through the sheet. A plurality of protrusions or teeth 425 are located adjacent slot 420. At the opposite end of stent 410 is second longitudinal edge 430 which has a plurality of apertures 435 located adjacent edge 430. In order to roll down the stent, second longitudinal edge 430 is coiled up and inserted in elongated slot 420 until the stent is tightly coiled to a reduced diameter form and slid onto the portion of a catheter. When the stent is loaded onto a balloon portion of a catheter, it has a low profile and can be easily transported through a body lumen and into, for example, the coronary artery. Once the stent is positioned in a coronary artery, the balloon portion of the catheter is radially expanded which in turn radially expands stent 410. As the stent expands, apertures 440 come in contact with teeth 425 and engage each other in an interlocking relationship. Stent 410 has tendency to return to its coiled state, thus, the interlocking relationship of the apertures and teeth prevent the stent from contracting.

The stent of the present invention, in particular the embodiments of FIGS. 19–29, are designed to engage in a sure manner, and, once engaged, to stay engaged with a high degree of reliability.

In all of the stent embodiments disclosed, it is desirable to minimize the protrusions that line the inner surface of the stent, to minimize the possibility of fibrin accumulation and thrombosis. To this end, the inner surface of the stent (the outermost edge) may have fewer rows of protrusions along the longitudinal edge, to maintain a smooth interior by minimizing the protrusions exposed inside the stent, that is, to minimize the number of protrusions that are not engaged.

The stent may be deployed in a vessel by any suitable means, such as with a stent delivery catheter formed from a angioplasty balloon catheter.

Again it should be understood that while in the above embodiments the protrusions on the body were formed from the body, in general the protrusions may be formed in any manner, including adding the protrusions to a smooth body made of the same or different material from the protrusions, or treating the body to create a roughened surface texture, with or without apertures in the body. As before, the surface texture forming the protrusions may be formed via plasma techniques, corona techniques, molding, casting, laser machining, etching, machining, extruding, or any other technique that changes the surface texture of the body.

Although in the preferred embodiment the stent of the present invention is deployed in a vessel with a balloon catheter, any suitable means for transporting and delivering the stent may be used. Furthermore, other modifications can be made to the present invention by those skilled in the art without departing from the scope thereof.

The stent of the present invention may be used not only in cardiovascular procedures, but also in urinary, prostate, renal, cerebral, nasal, auditory, rectal procedures and other medical procedures.

Furthermore, it should be understood that any dimensions set forth for the above embodiments are not intended to limit the invention to only those dimensions. For example, while certain dimensions might be appropriate for a stent used in a coronary artery, these same dimensions might not be suitable for a stent used in other areas of a patient's vasculature or body lumen. It is also understood that the drawings are not necessarily to scale.

Other modifications can be made to the present invention by those skilled in the art without departing from the scope thereof.

We claim:

1. An intraluminal stent implantable in a body lumen, comprising:

a substantially cylindrical body portion having a length extending along a longitudinal direction, the body portion having a first edge containing a slot extending along the longitudinal direction, and the body portion having a second edge extending along the longitudinal direction;

the second edge passing through the slot;

a third edge and a fourth edge each having a plurality of teeth for engaging the slot in interlocking relationship;

wherein when the cylindrical body portion is expanded from a first reduced diameter to a second, enlarged diameter, the plurality of teeth engage the slot in an interlocking relationship to thereby hold the stent in the second, enlarged diameter configuration.

* * * * *